(12) United States Patent
Beri

(10) Patent No.: US 10,987,083 B2
(45) Date of Patent: Apr. 27, 2021

(54) ULTRASOUND TRANSDUCER HOLDER

(71) Applicant: Serena Beri, Westford, MA (US)

(72) Inventor: Serena Beri, Westford, MA (US)

( * ) Notice: Subject to any disclaimer, the term of this patent is extended or adjusted under 35 U.S.C. 154(b) by 495 days.

(21) Appl. No.: 15/982,673

(22) Filed: May 17, 2018

(65) Prior Publication Data

US 2019/0053784 A1 Feb. 21, 2019

Related U.S. Application Data

(60) Provisional application No. 62/547,243, filed on Aug. 18, 2017.

(51) Int. Cl.
| | |
|---|---|
| *A61B 8/00* | (2006.01) |
| *A61B 8/14* | (2006.01) |
| *A61B 8/08* | (2006.01) |
| *B25J 18/06* | (2006.01) |
| *B25J 9/14* | (2006.01) |

(52) U.S. Cl.
CPC .............. *A61B 8/4218* (2013.01); *A61B 8/14* (2013.01); *A61B 8/0883* (2013.01); *A61B 8/4227* (2013.01); *A61B 8/4254* (2013.01); *A61B 8/4427* (2013.01); *A61B 8/5207* (2013.01); *B25J 9/142* (2013.01); *B25J 18/06* (2013.01)

(58) Field of Classification Search
CPC ....... A61B 8/0883; A61B 8/14; A61B 8/4218; A61B 8/4227; A61B 8/4254; A61B 8/4427; A61B 8/5207; B25J 18/06; B25J 9/142
See application file for complete search history.

(56) References Cited

U.S. PATENT DOCUMENTS

| | | | |
|---|---|---|---|
| 3,954,098 | A | 5/1976 | Dick et al. |
| 4,106,492 | A | 8/1978 | Schuette et al. |
| 4,222,274 | A | 9/1980 | Johnson |

(Continued)

OTHER PUBLICATIONS

"Cornell University engineers 3D print soft actuator that mimics the muscles of octopus tentacles," <www.3ders.org>, retrieved May 7, 2018 (4 pages).

(Continued)

*Primary Examiner* — Amelie R Davis
(74) *Attorney, Agent, or Firm* — Clark & Elbing LLP

(57) ABSTRACT

Described herein are devices and methods useful in automating ultrasound imaging. The device include a base coupled with soft robotics, which may be attached to an ultrasound transducer probe in order to robotically manipulate the probe to perform an ultrasound scan. The device has an adjustable structure configured to hold the probe on a walking soft robot. The device can be configured to be attached to, or worn by, the patient. With soft robotic actuation and locomotion, the holder can move and position the probe during a real time ultrasound scanning procedure. Furthermore, the holder may be equipped with sensors to sense and map pressure and location. The position of the holder can be robotically monitored and controlled so as to achieve consistency and reproducibility between ultrasound scans. Due to the wearable nature of the holder, the scans may be conducted while the patient is in motion, thereby providing a portable solution for ultrasonic imaging. The holder is cost effective and may be used in conjunction with various ultrasound probes.

22 Claims, 20 Drawing Sheets

(56) References Cited

U.S. PATENT DOCUMENTS

| | | | |
|---|---|---|---|
| 4,317,370 A | 3/1982 | Glenn | |
| 6,261,231 B1* | 7/2001 | Damphousse | A61B 8/4209 600/437 |
| 9,464,642 B2 | 10/2016 | Ilievski et al. | |
| 2008/0021317 A1* | 1/2008 | Sumanaweera | A61B 8/4281 600/437 |
| 2014/0109560 A1* | 4/2014 | Ilievski | B25J 9/142 60/327 |

OTHER PUBLICATIONS

"Echo Blaster 128 family scanners," Telemed, <www.pcultrasound.com/products/products_eb128/index.html>, retrieved Apr. 29, 2020 (2 pages).

"Improve Robot Balance and Grip with FlexiForce," Tekscan, <www.tekscan.com/print/applications/improve-robot-balance-and-grip-flexiforce>, retrieved Apr. 29, 2020 (3 pages).

"Revolutionizing General-Purpose Photoelectric Sensors," Keyence, <www.keyence.com/products/sensor/photoelectric/pr-g>, retrieved Apr. 29, 2020 (3 pages).

"Soft 3D Printed Robot Traverses Sand, Enters Your Nightmares," All3DP, <all3dp.com/soft-body-3d-printed-robot/>, retrieved Jun. 25, 2020 (5 pages).

"Travel Circular Motion Linkage." Yahoo Image Search Results, <images.search.yahoo.com/search/images;_ylt=AwrDQ2o2o2tZ9VoA14X7w8QF?p=travel+circular+motion+linkage&fr=mcafee&fr2=p%3As%2Cv%3Av%2Cm%3Apivot#id=79&iurl=https%3A%2F%2Fs-media-cache-ak0.pinimg.com%2Foriginals%2F78%2F39%2F32%2F7839323e6ce3eba88bc120a1dd9135e0.gif&action=click>, retrieved Apr. 29, 2020 (3 pages).

Da Cruz et al., "Left Ventricle Assessment—Ejection Fraction and Stroke Volume Through Simpson' Method and 3D Transthoracic Echocardiography in Patients with Aortic Valve Disease," J Cardiol and Curr Res. 2(5) (2015) (6 pages).

De Falco, "Multi-Module Variable Stiffness Manipulator," Soft Robotics Toolkit, <softroboticstoolkit.com/mmvsm/design>, retrieved Apr. 29, 2020 (3 pages).

Gelli, "IQ Probes," Esaote, retrieved May 7, 2018 (8 pages).

Ihnatsenka et al., "Ultrasound: Basic understanding and learning the language," Int Jour Shoulder Surg. 4(3):55-62 (2010) (19 pages).

Lu et al., "Ergonomic Ultrasound Device," Dept of Biomed Eng., University of Wisconsin-Madison (2004) (29 pages).

Maret et al., "Computer-assisted determination of left ventricular endocardial borders reduces variability in the echocardiographic assessment of ejection fraction," Cardiovas Ultra. 6(55) (2008) (14 pages).

Ren et al., "Human-Compliant Body-Attached Soft Robots Towards Automatic Cooperative Ultrasound Imaging," 2016 20th IEEE International Conference on Computer Supported Cooperative Work in Design (CSCWD 2016), May 4-6, Nanchang, China, (2016) (7 pages).

Wiguna, "3D-Printed Arduino Spider Robot" and video transcript, YouTube, <www.youtube.com/watch?v=9Pos9pE8xwU>, retrieved Apr. 29, 2020 (3 pages).

Yang et al., "Proceedings," The Hamlyn Symposium on Medical Robotics, Imperial College London and the Royal Geographical Society, Jun. 25-28, 2016, (124 pages).

* cited by examiner

Prior Art

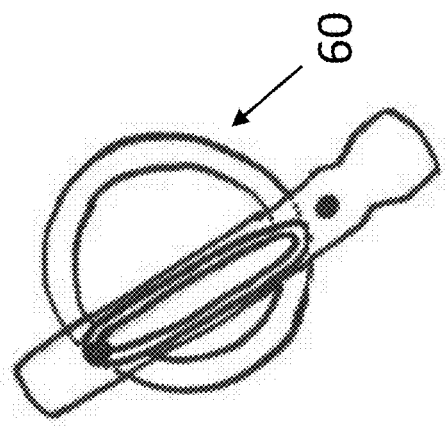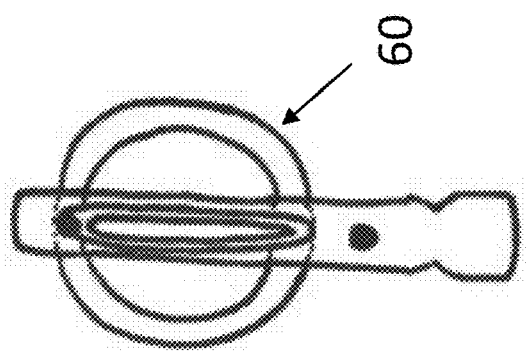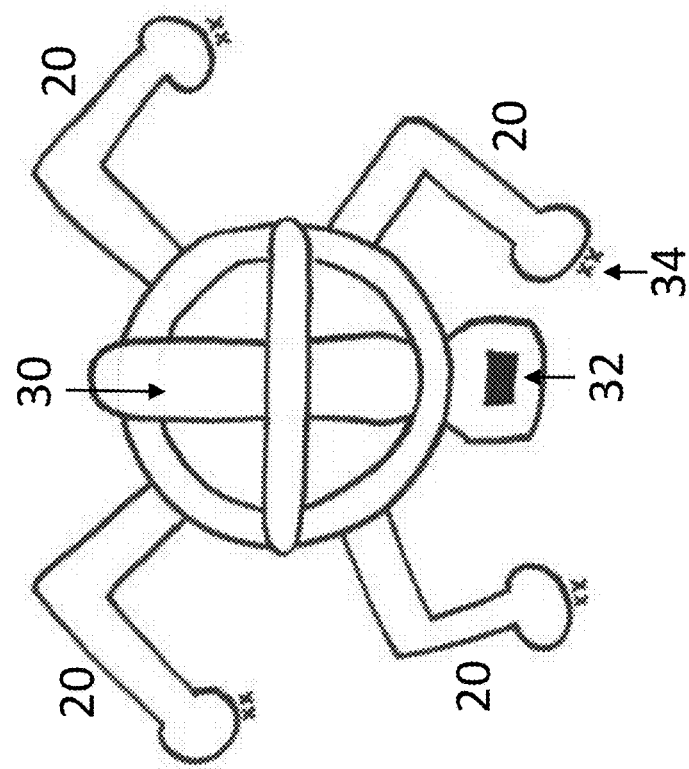
FIG. 3B
FIG. 3A

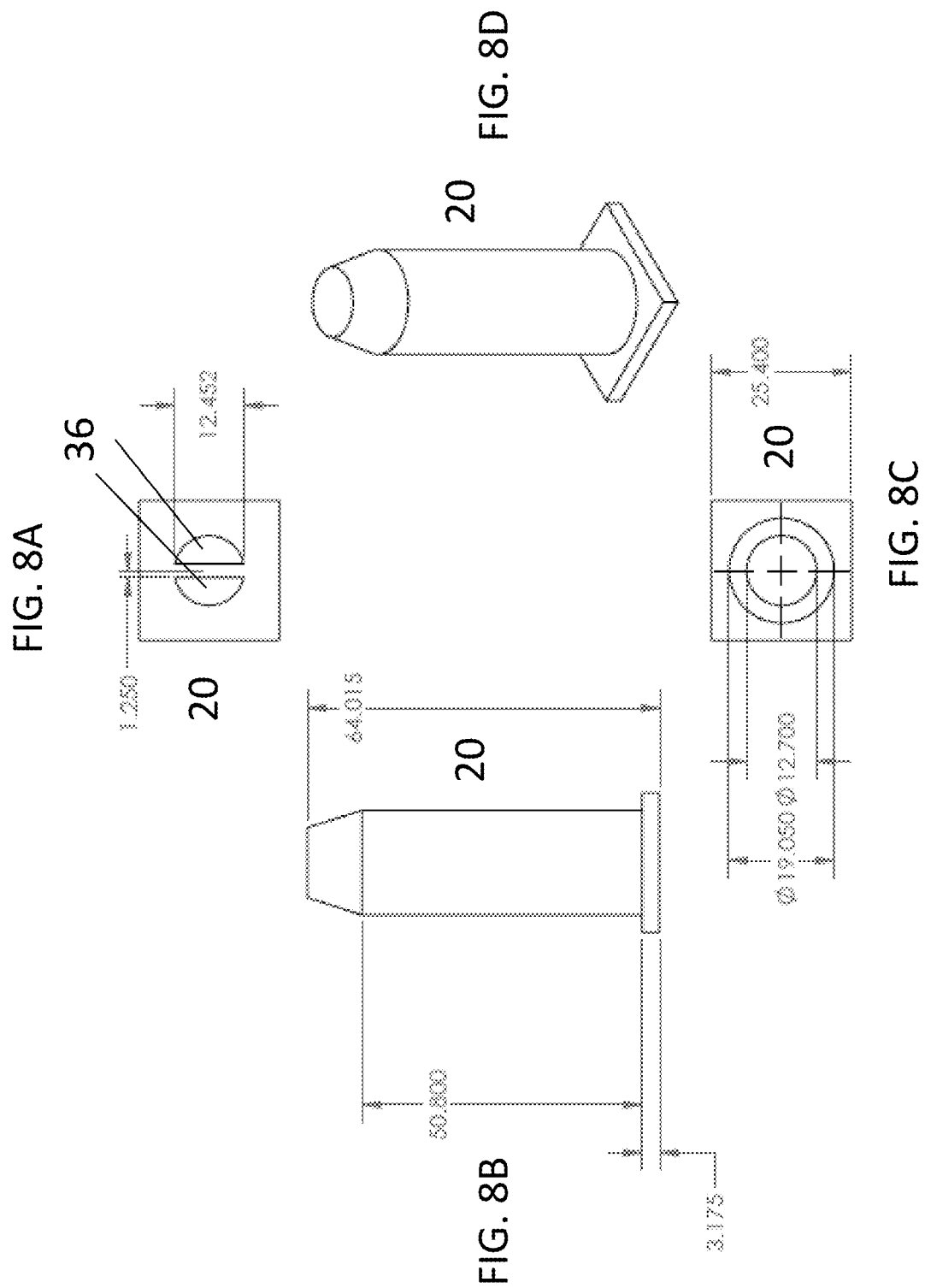

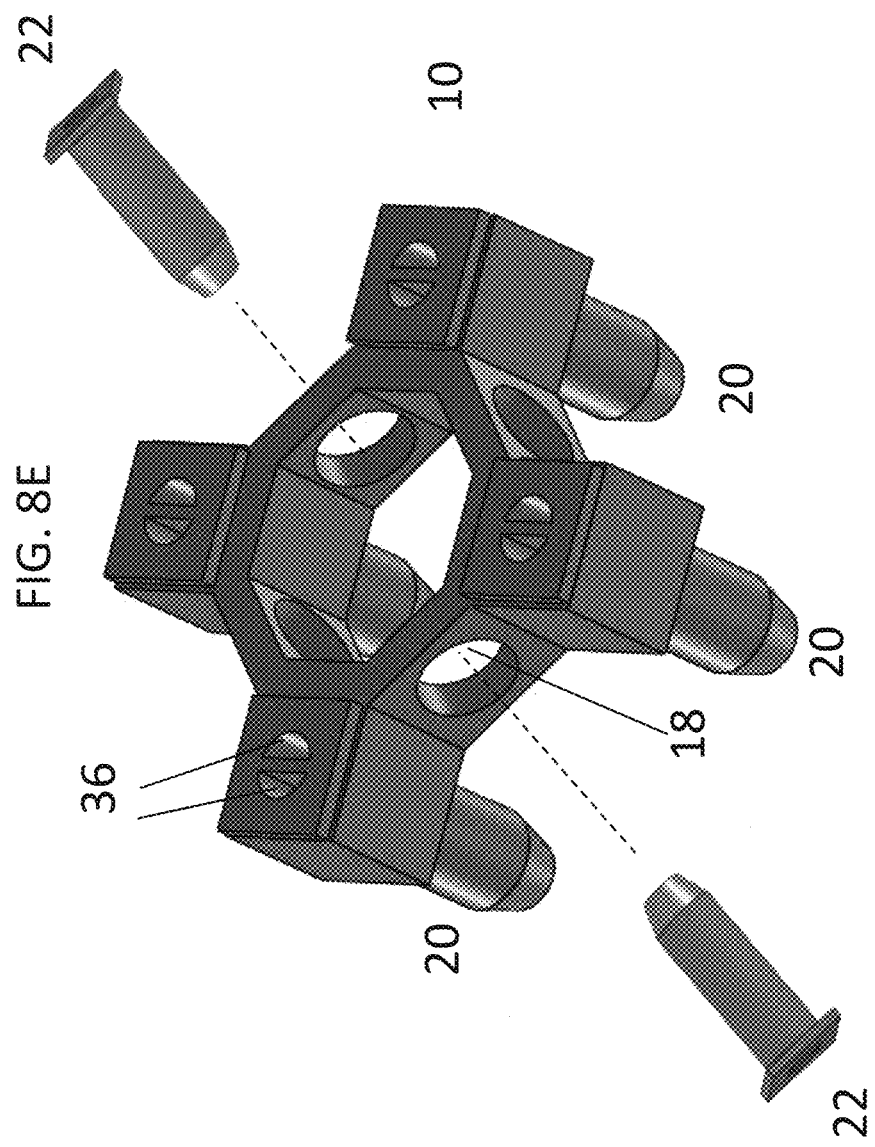

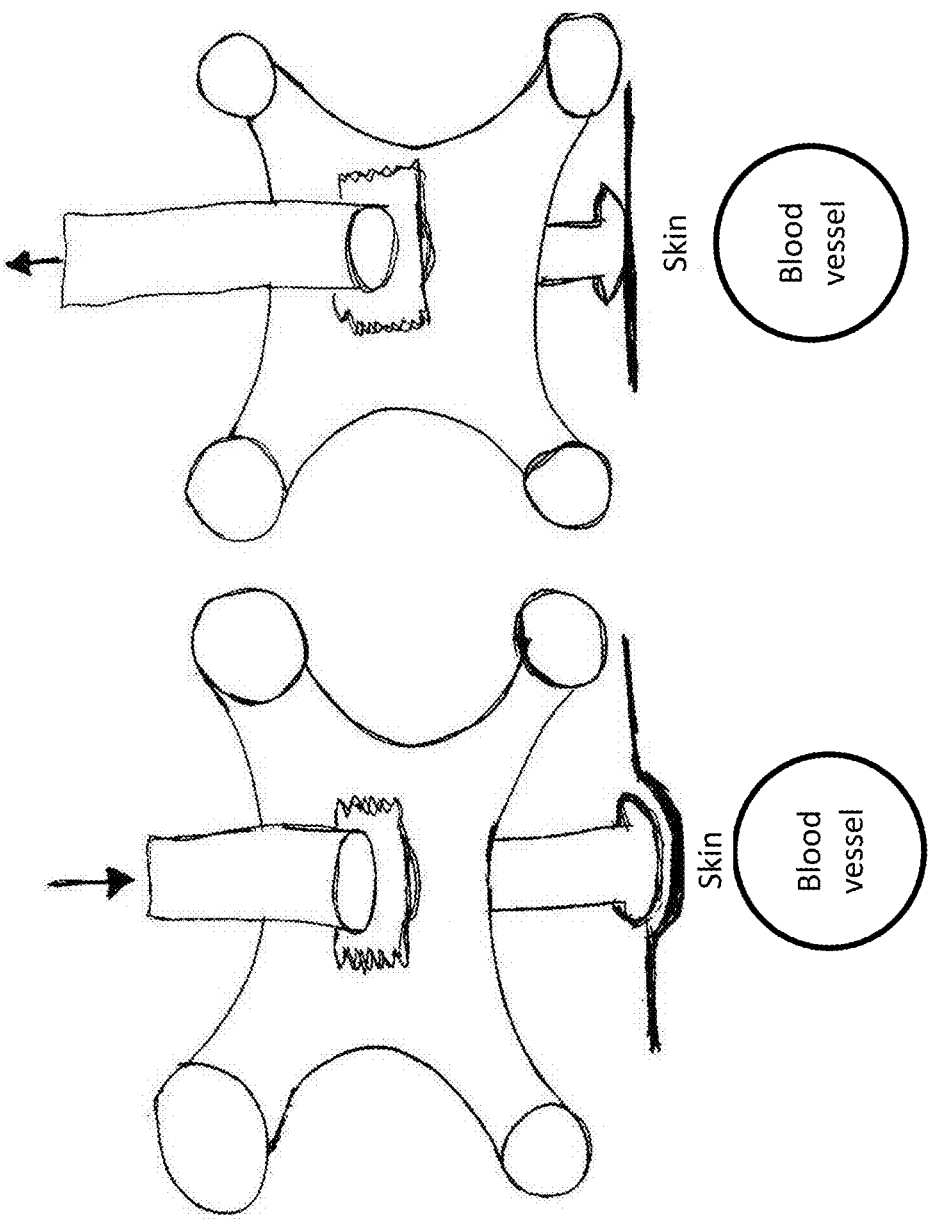

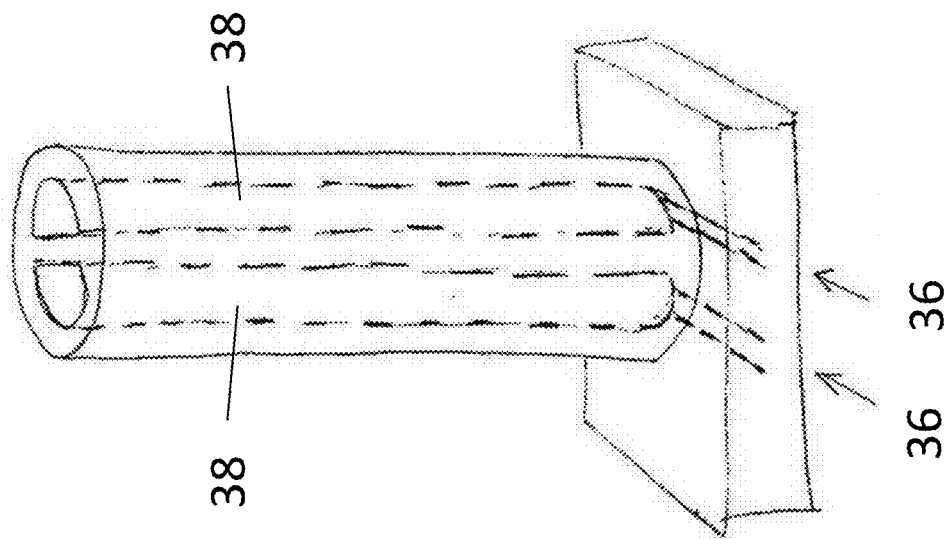

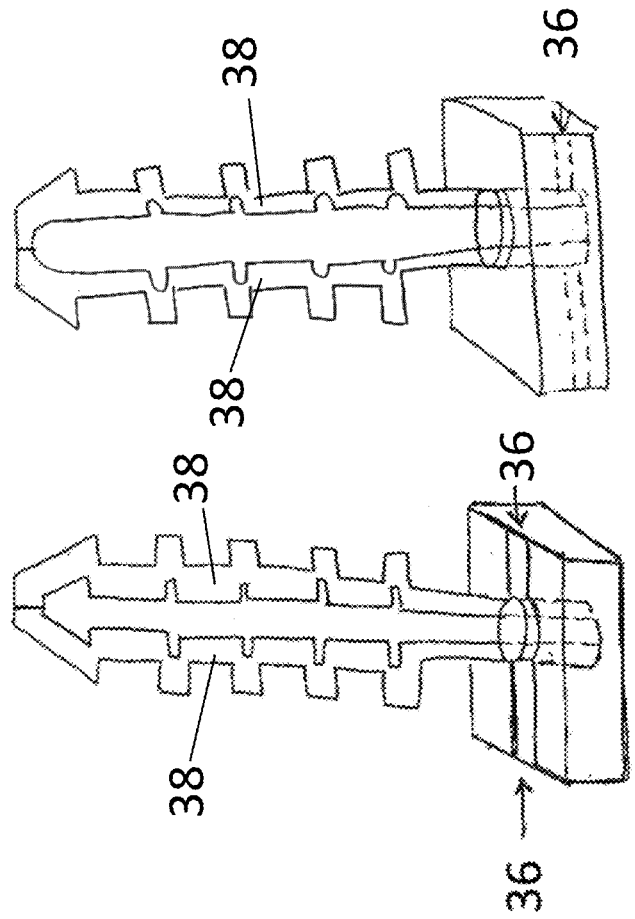

ULTRASOUND TRANSDUCER HOLDER

BACKGROUND OF THE INVENTION

Ultrasound imaging is a routine method for probing the human body and for use in various diagnostic tests. Generally, an ultrasound transducer is manually placed onto the body by a technician (a sonographer) and an image is viewed in real time on a monitor (FIGS. 1A-1B). After viewing the image, the technician then moves the probe to obtain a desired image scan. Due to its manual nature, the output of an ultrasound procedure is highly dependent on the experience and capability of the technician performing the procedure. The results from an ultrasound procedure are not always reproducible between different technicians or scans. Furthermore, the manual process can be tiring for the technician and can cause musculoskeletal disorders due to sustained forces applied in unnatural positions. Thus, a need exists for an ultrasound device that can automate the process of performing ultrasound imaging in order to achieve uniform, consistent, and reproducible ultrasound images.

SUMMARY OF THE INVENTION

Described herein are devices and methods useful in automation of ultrasound imaging. In one aspect, the invention features an ultrasound transducer holder including a base for holding and/or positioning an ultrasound transducer, and one or more (e.g., 2, 3, 4, 5, 6, 7, 8, 9, or 10) actuatable arms attached to the base. The actuatable arm includes a flexible molded body having a plurality of interconnected chambers disposed within the molded body, and a pressurizing inlet that is configured to receive fluid into the plurality of interconnected chambers, such that the molded body is configured to expand when the plurality of interconnected chambers are pressurized by the fluid, thereby moving the base and/or the transducer upon actuation of the arm. The ultrasound transducer holder may further include an ultrasound transducer contacting the base, to form an ultrasound transducer assembly. The holder or assembly is portable and can be attached to or wearable on the body. The transducer may be affixed to the base (e.g., with a strap, VELCRO®, snaps, friction fit, fastener, or other retaining mechanism). The holder or assembly may be affixed to a patient (e.g., a human patient) with a strap, VELCRO®, snaps, friction fit, fastener, or other retaining mechanism.

The actuatable arms of the ultrasound transducer holder include a flexible molded body having an elastically extensible material and a strain-limiting material having a higher elastic modulus relative to the elastically extensible material.

The base of the ultrasound transducer holder may be composed of a rigid material (e.g., plastic) and may also include a center hole that is sized (e.g., 10-100 mm) and shaped (e.g., circle, square, hexagon, or octagon) to surround or fit a transducer. The holder may further include a top frame attached to the base. The top frame and the actuatable arms may be adjustable in height. The top frame may include a rotary guide frame, which can control the rotation angle of the ultrasound transducer. The ultrasound transducer holder may further include a sensor, such as a pressure sensor or photo sensor. The pressure sensor may be located on the one or more actuatable arms. The photo sensor may be located on the ultrasound transducer. The ultrasound transducer holder may further include a microprocessor, for example, to control the actuatable arms or to manipulate the holder in order to move the ultrasound transducer to achieve a desired ultrasound parameter (e.g., pressure, alignment, rotation angle, or tilt angle). The holder is configured to achieve a tilt angle of the transducer that may vary between about 0.1° and 30° and the holder is configured to produce a rotation angle of between 0° and 360°.

In another aspect, the invention features a method of performing an ultrasound procedure (e.g., an echocardiogram) using the ultrasound holder of any of the above aspects with an ultrasound transducer. The method includes providing the ultrasound holder assembly, initiating a series of pressurizations and depressurizations in the actuatable arm(s) that bring the ultrasound transducer into contact with a target object (e.g., a subject), and emitting ultrasound waves from the transducer to image the target object. The series of pressurizations and depressurizations may adjust a height, pressure, alignment, rotation angle, or tilt angle of the holder, and, thus, the transducer, relative to the target object. The series of pressurizations and depressurizations may also move the transducer along a target object. The method may be used to manipulate the holder in order to move the ultrasound transducer to achieve a desired ultrasound parameter (e.g., one or more of pressure, alignment, rotation angle, and tilt angle).

In the methods described above, the ultrasound procedure may be used to produce an echocardiogram of a patient's heart or a musculoskeletal image. The echocardiogram may be used to determine size, shape, and motion of the patient's heart. The echocardiogram may show images of four chambers of the heart, heart valves, walls of the heart, blood vessels entering and exiting the heart, and/or the pericardium of the heart (e.g., while in motion). The ultrasound procedure may be used in real-time imaging in motion scenarios, such as during musculoskeletal diagnosis, prediction, and/or ultrasonic therapy for chronic musculoskeletal disorders. The ultrasound procedure may also be used during pandemic, epidemic, or contagious disease control scenarios where the ultrasound scans can be conducted without the need for direct healthcare professional or technologist intervention or contact with the patients (e.g., autonomously, such as without (or with minimal) human intervention (in particular, controlled by a computer)).

In another aspect, the invention features a kit comprising the ultrasound transducer holder of any of the above aspects and an ultrasound transducer. The kit may further include instructions for combining the ultrasound transducer holder and the ultrasound transducer to produce an ultrasound transducer assembly or instructions for using one or more of the transducer holder, the ultrasound transducer, or the ultrasound transducer assembly.

BRIEF DESCRIPTION OF THE DRAWINGS

FIG. 3A is a schematic drawing of an automated mapping walking soft robotic spider holding an ultrasound transducer. Shown is photo sensor (32) on transducer probe (30) and pressure mapping sensor (34) on actuatable arm (20).

FIG. 3B is a schematic drawing of a rotary guide frame shown in two different orientations. The rotary guide frame can control the circular motion of the ultrasound transducer.

FIGS. 8A-8E are schematic drawings showing multiple perspectives of a soft robotic actuatable arm with dimensions labeled in mm. FIG. 8A is a top view of actuatable arm (20). FIG. 8B is a side view of actuatable arm (20). FIG. 8C is a bottom view of actuatable arm (20). FIG. 8D is an elevation view of actuatable arm (20). FIG. 8E is an exploded view showing the location of linear actuators (22), which can fit into hole/recess (18) of base (10).

With reference to FIGS. 11A-11B, the angles shown correspond to the movement of a transducer that is held in top frame (16). The angular position of the transducer held within hexagonal hole (12) of base (10) is adjusted by actuation of horizontal actuatable arms positioned within hole/recess (18). Measured lengths are in millimeters (mm).

FIG. 13A shows the transducer probe (30) contacting the base (40).

FIGS. 14A-14B are schematic drawings illustrating a holder and a transducer moving in a downwards (FIG. 14A) and upwards (FIG. 14B) motion to image a blood vessel underneath the skin.

FIGS. 15A-15C are schematic drawings of actuatable arms. FIG. 15A shows an actuatable arm with pressurizing air inlet (36). By filling one or both air chambers (38), the actuatable arms can bend or elongate. FIGS. 15B-15C show alternative types of baffle actuators with air inlets (36) and air chambers (38).

DETAILED DESCRIPTION

Described herein are devices and methods to perform automated ultrasound imaging using soft robotic technology. The devices feature an ultrasound transducer holder with a base for holding an ultrasound transducer and at least one or more (e.g., 2, 3, 4, 5, or more, in particular, 4) actuatable arms attached to the base. The actuatable arm has a flexible molded body with a plurality of interconnected chambers disposed within the molded body. The actuatable arm contains a pressurizing inlet to receive a fluid (e.g., air) into the interconnected (e.g., semicircular) chambers. When the fluid (e.g., air) pressurizes the chambers, it actuates the arm, causing the base to which it is attached to move. The transducer holder can be connected to an ultrasound transducer in order to perform ultrasound imaging on a subject (e.g., a human).

Figure 2:
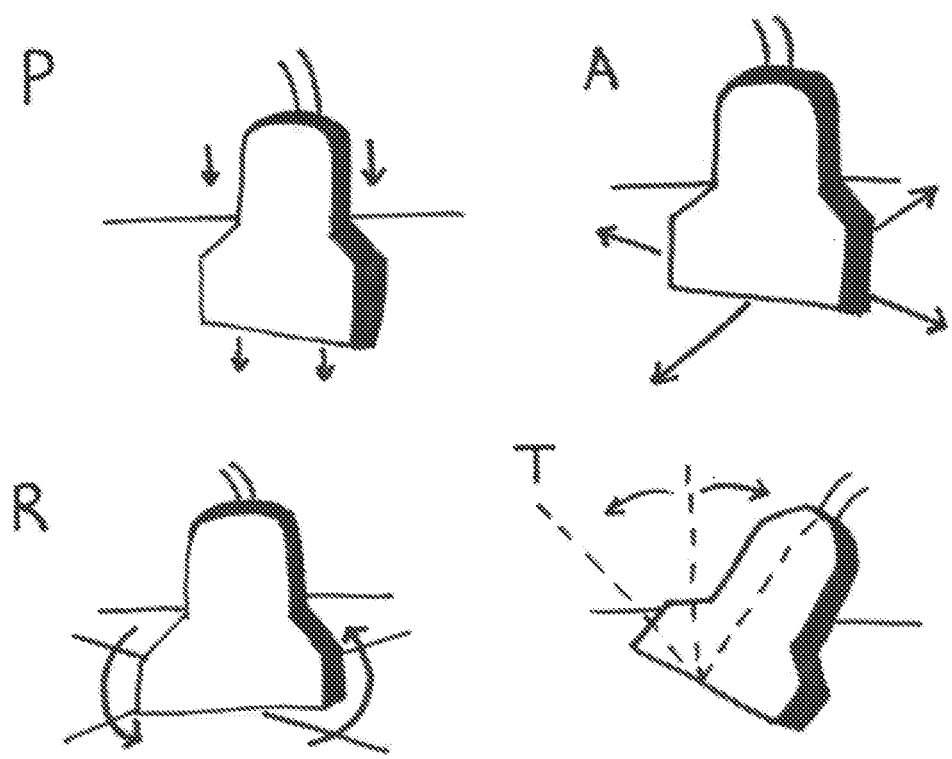
FIG. 2 is a schematic drawing adapted from Ihnatsenka et al. (Int. Jour. Shoulder Surg., 4:55-62, 2010), showing the four parameters of ultrasound: pressure, alignment, rotation, and tilt.

The soft robotic transducer holder can be used to manipulate a transducer probe along four physical parameters when performing an ultrasound scan: pressure, alignment, rotation, and tilt (FIG. 2). The ultrasound transducer holder produces reproducible ultrasound images when used during an ultrasound procedure. Ultrasound imaging can be automated when using the ultrasound imaging holder, eliminating or reducing the need for, or involvement of, a technician to manipulate the ultrasound transducer during the ultrasound procedure. The methods may help to enhance reproducibility and minimize variation between scans. Additionally, the proposed automation solution and ergonomic designs eliminate the potential for musculoskeletal disorders in sonographers due to sustained forces applied in unnatural positions. The automation solution also allows for increased efficiency in performing an ultrasound scan by reducing user error(s) and reduces the risk of injury or tiredness. Other advantages of using the holder include use as a training device for new technicians to guide them on proper placement and pressure of the ultrasound probe.

Ultrasound Imaging

Ultrasound imaging is a diagnostic imaging technique that uses sound waves with frequencies that are higher than 20 kHz (e.g., higher than 2 megahertz), the audible limit of human hearing. The technique works by producing a high frequency sound wave, which is focused by the shape of an ultrasound transducer, a lens on the transducer, or a complex set of control pulses from the ultrasound scanner. The sound waves then travel into the body and are reflected from the various layers and structures inside the body. The reflections produce echoes, which are received by the transducer, which then takes the vibrations and converts them into a digital image. The short wavelength of the sound waves allows resolution of small internal details in structures and tissues in high resolution. Therefore, ultrasound imaging is useful in medicine for diagnostic and therapeutic purposes. Ultrasound is a well-established technique that has been described, for example, in Ihnatsenka et al. (Int. Jour. Shoulder Surg. 4:55-62, 2010) and U.S. Pat. Nos. 4,222,274 and 4,317,370, the disclosures of which are hereby incorporated by reference in their entirety.

To collect a useful ultrasound scan, a technician manipulates the transducer to achieve the correct pressure, alignment, rotation angle, and tilt angle on the skin.

Ultrasound transducers, also known as probes, can be transmitters, receivers, or transceivers. Transducers can convert electrical signals into ultrasound, convert ultrasound into electrical signals, or both. They emit or receive signals, and can reconstruct an image by calculating the time between emission, reflection, and receipt of ultrasound signals.

An echocardiogram is one type of diagnostic test that uses ultrasound imaging. An echocardiogram is used to image different parts of the heart. This can be used to probe the structure and function of the heart, check the thickness and movements of the heart wall, observe the heart valves, measure the size and shape of the heart's chambers, and check the ability of the heart chambers to pump blood. Furthermore, an echocardiogram may be used to detect a disease (e.g., cardiomyopathy) or look for blood clots. Echocardiogram technology has been described, for example, in Armstrong, William F., and Thomas Ryan (Feigenbaum's echocardiography. Lippincott Williams & Wilkins, 2012), and U.S. Pat. Nos. 3,954,098 and 4,106,492, the disclosures of which are hereby incorporated by reference in their entirety. Furthermore, automated processes, artificial intelligence, and computational software have been used to optimize echocardiograms. This is described, for example, in Maret et al. *Cardiovasc. Ultrasound* 6:55, 2008, which is hereby incorporated by reference in its entirety. The devices and systems described herein improve on this process by optimizing the orientation of the ultrasound transducer within the ultrasound holder. Exemplary ultrasound transducer probes are manufactured by, e.g., Telemed (e.g., PV 6.5/10/128Z-3), Philips Medical, Promed, and Easote, incorporated herein by reference.

Ultrasound Transducer Holder

Figure 4B:
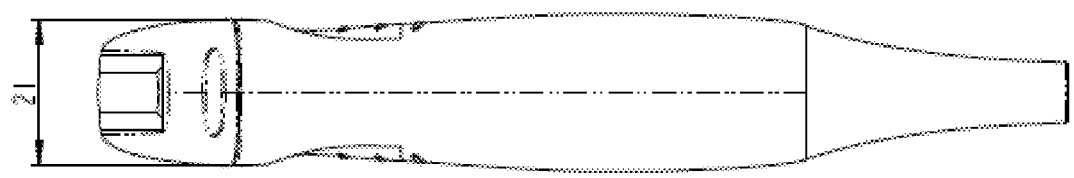
FIGS. 4A-4B are schematic drawings of a Telemed PV 6.5/10/128Z-3 ultrasound transducer showing dimensions in mm of the front (FIG. 4A) and side (FIG. 4B) views.
Figure 4A:
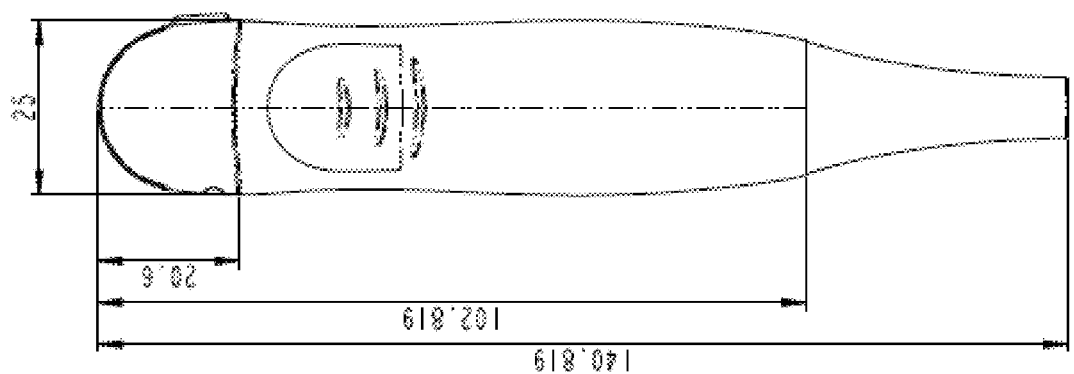
Figure 5:
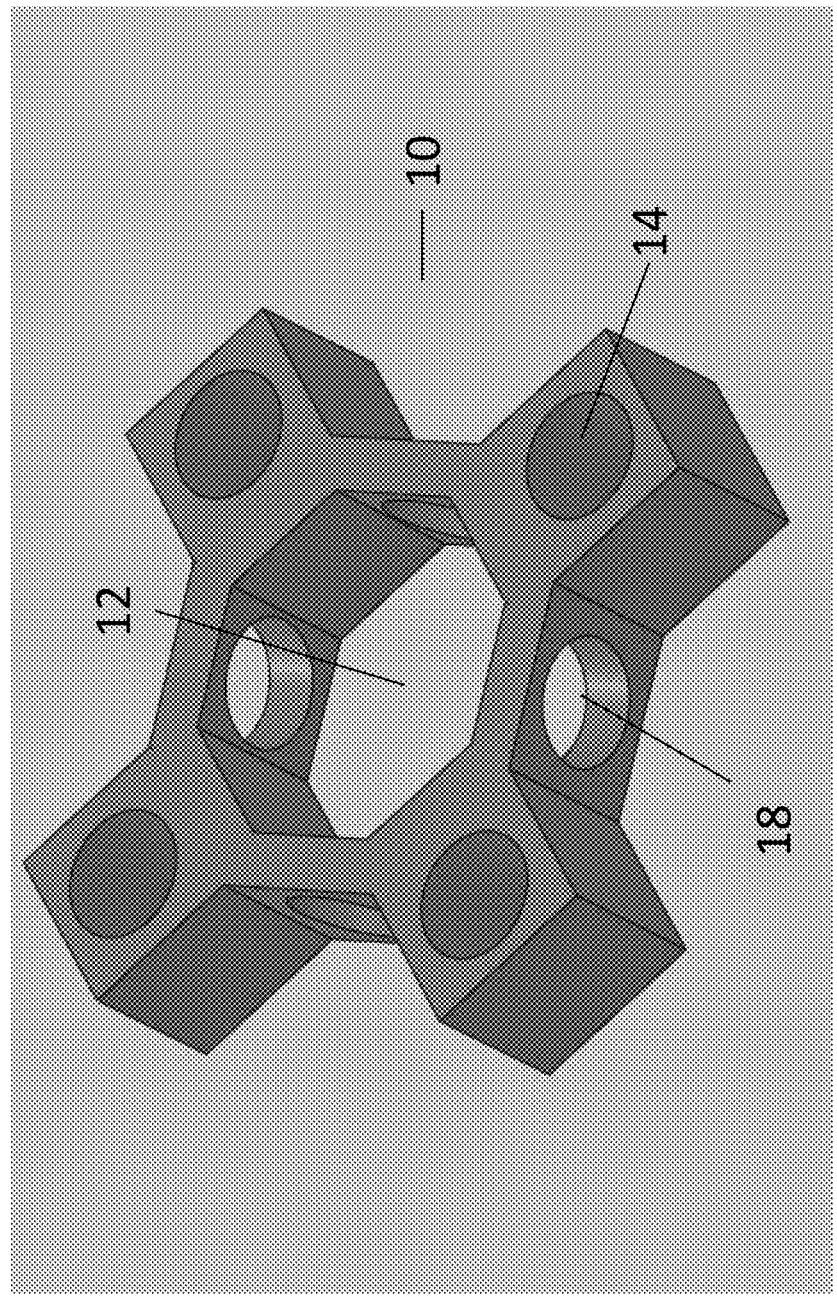
FIG. 5 is a schematic drawing of an ultrasound base (10) configured to hold an ultrasound transducer. Center hole (12) has an octagon shape into which the transducer can fit. The outer cubic protrusions contain cylindrical recesses (14) into which the soft robotic actuatable arms can fit for vertical locomotion. Other cylindrical recesses/holes (18) are shown into which the linear soft robotic actuatable arms fit for moving the probe in the octagon center hole (12)
Figure 6A:
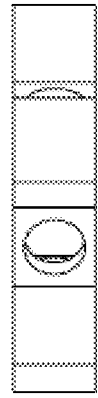
FIGS. 6A-6C are schematic drawings showing a side view (FIG. 6A), an elevation view (FIG. 6B) and top view (FIG. 6C) of the base (10) showing dimensions in mm.
Figure 6C:
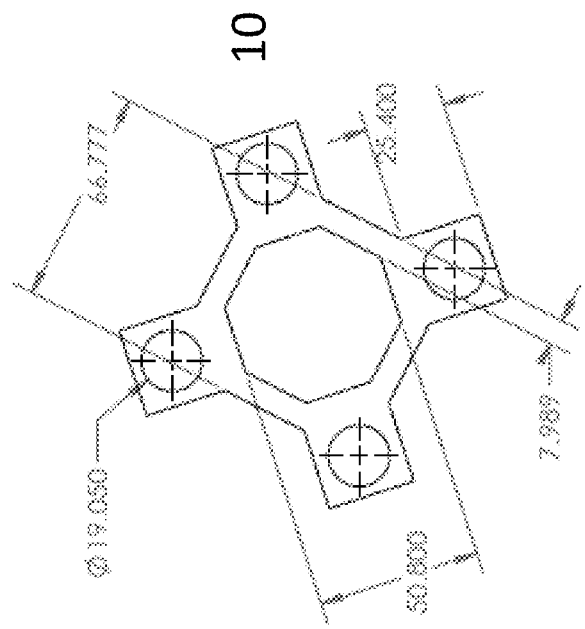
Figure 6B:
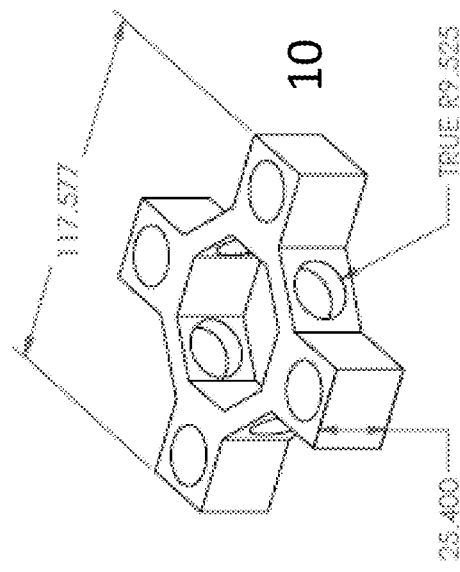

The devices described herein include a soft robotic holder including base (10), which supports ultrasound probe (30) on one or more (e.g., four) actuatable arms (20) (e.g., as a walking soft robot (FIG. 3A)). The robotic holder is configured to position ultrasound probe (30) during an ultrasound imaging procedure. The robotic holder can be adjusted to adapt to various sizes and shapes of available probes (FIGS. 4A-4B). Probe (30) may be held in top frame (16) attached to base (10) and soft robotic actuators (20, 22) from the bottom or sides can move probe (30) to the desired position or angle (FIG. 3B). The location of probe (30) can be measured with respect to the frame via photo sensors (32), which can be attached to probe (30), arms (20) or base (10).

The ultrasound holder may also contain a pressure mapping system, which can be located, e.g., on the bottom of soft robot arm (20). Transducer probe (30) may also function as a pressure mapping probe. For example, probe (30) or sensor (34) on the probe can measure pressure applied and/or maintain steady pressure for accurate imaging over an extended period of time.

Figure 13B:
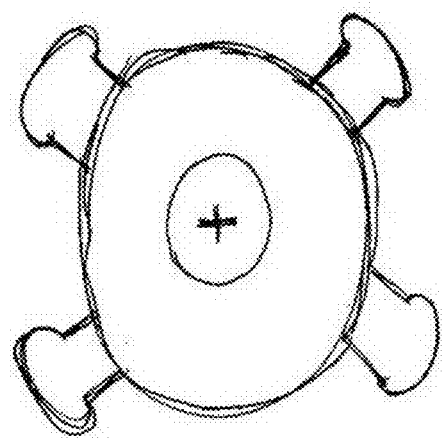
FIGS. 13A-13B are schematic drawings illustrating a side view (FIG. 13A) and top view (FIG. 13B) of exterior ergonomic shapes of the transducer holder assembly with base (40) and actuatable arms (50).
Figure 13A:
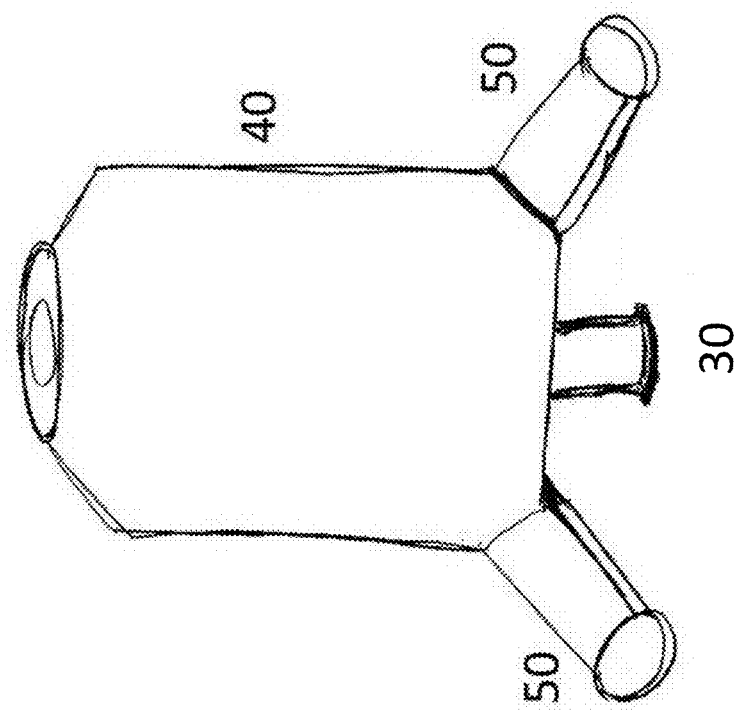
Figure 16:
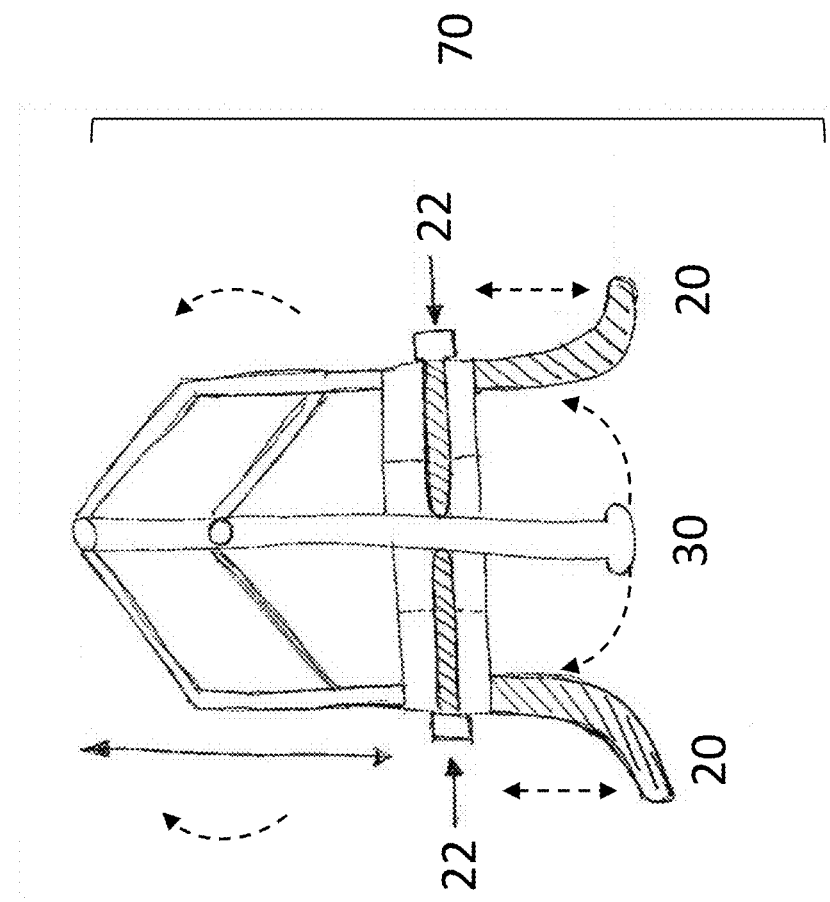
FIG. 16 is a schematic drawing of ultrasound transducer assembly (70) with locomotive actuators (20), linear actuators (22) and probe (30). Locomotive actuators (20) can be used to adjust the vertical alignment (e.g., up or down) of transducer assembly (70), while linear actuators (22) can be used to adjust the angular position (e.g., relative to a target surface) of probe (30).

Soft robotic locomotion can be used to move a transducer probe around and conduct automated ultrasound scanning. The height of the soft robot can be adjusted so that it can impart various pressures and tilt positions. The holder can be configured to maintain the probe in a stationary position when taking images or can be configured to change position and orientation of the probe to various locations during or between imaging. FIG. 16 shows how the probe is held in place in the assembly. Linear actuators (22) are arranged horizontally and push on probe (30), to alter its angle. The holder may be portable, wearable, dynamic, maneuverable, and ergonomic (FIGS. 13A-13B). The components of the ultrasound transducer holder are described below.

Base

Figure 11B:
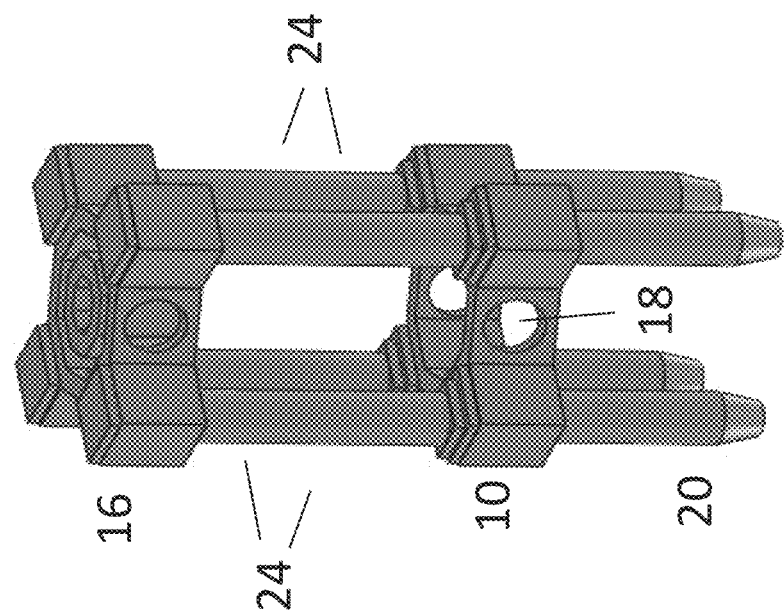
FIGS. 11A-11B are schematic drawings showing a top perspective view (FIG. 11A) and side perspective view (FIG. 11B) of base (10) connected to four actuatable arms (20) and top frame (16) that can control the height of an ultrasound transducer. Top frame (16) rides on the four pillars (24) and may be adjustable in height and can be locked at various heights (e.g., using stop screws or height-adjusting actuators).
Figure 11A:
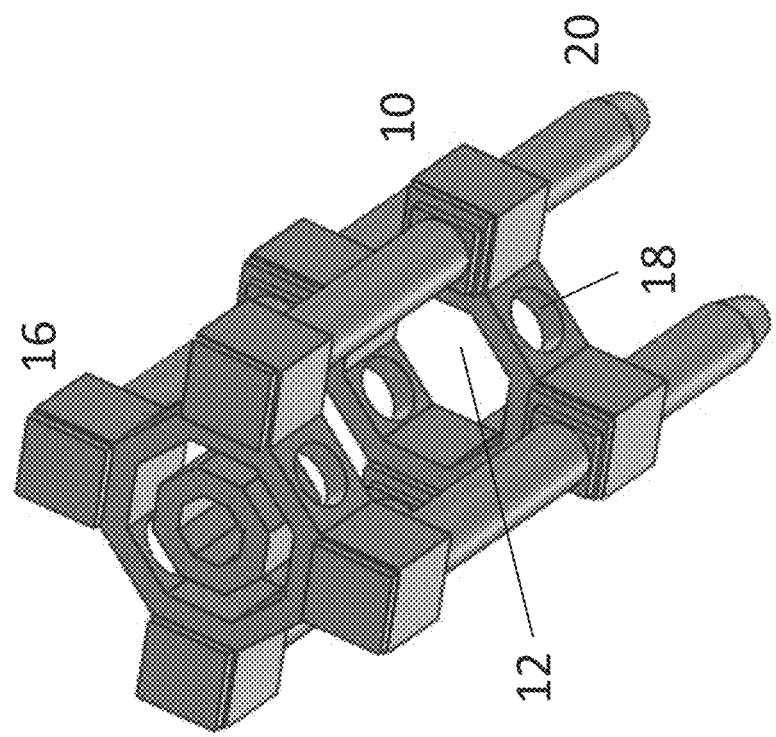
Figure 12A:
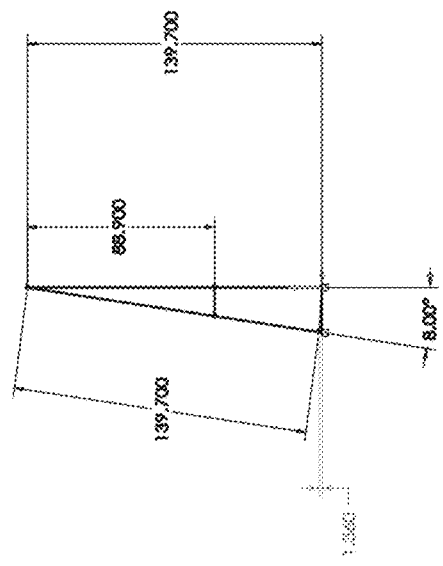
FIGS. 12A-12D are schematic drawings illustrating 4° (FIG. 12A), 8° (FIG. 12B), 12° (FIG. 12C), and 16° (FIG. 12D) tilt angles of the ultrasound transducer holder.
Figure 12B:
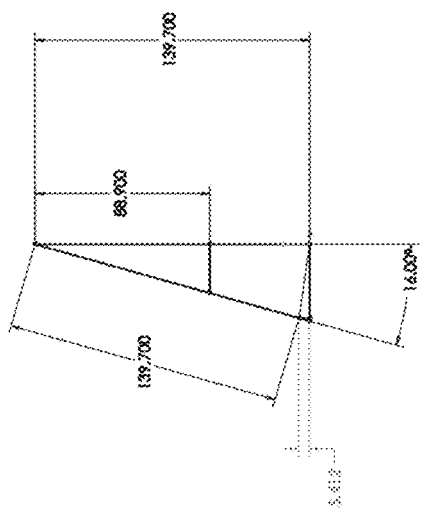
Figure 12C:
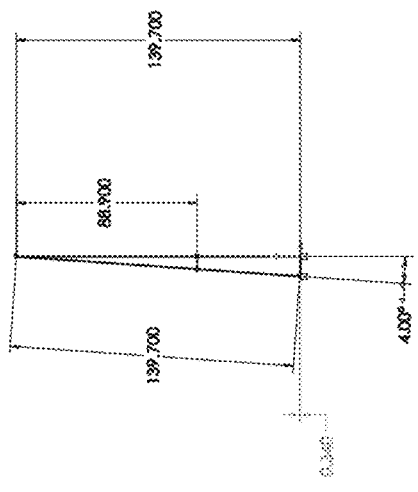
Figure 12D:
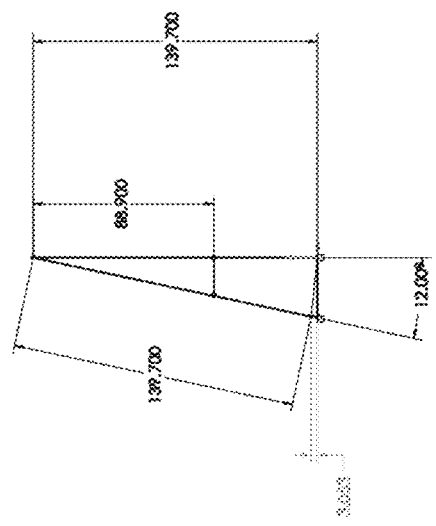

Base (10) of the holder (FIGS. 5, 6A-6C) may be made of any light and rigid material (e.g., plastic, such as acrylonitrile butadiene styrene (ABS)), and is configured for holding the soft robotic elements and probe (30). Base (10) may also support top frame (16) (see, e.g., FIGS. 11A-11B), which can be used to hold transducer probe (30) in place. Base (10) may contain center hole (12) that is sized and shaped (e.g., circle, square, hexagon, and octagon) to accommodate transducer probe (30). Hole (12) may have a diameter of 10 mm to about 100 mm. Each side of the base may be, for example, from about 10 mm to about 30 cm.

Soft Robotic Actuators (Linear and Locomotive)

Transducer base (10) contains soft robotic actuators connected to or integrated into base (10). The actuators include air inlets (36) and may include multiple internal fluid (e.g., air) channels (38) (FIGS. 15A-15C). For example, actuatable arm (20, 22) may be cylindrical in shape with two semicircular air channels (38) or chambers. By actuating one of the channels, it may cause the arm to bend. By inflating the other channel, it may cause the arm to bend in the opposite direction. By inflating both channels (38), it may cause the arm to elongate. The actuatable arms may be from about 10 mm to about 20 cm (e.g., 100 mm, 200 mm) long. Soft robotic actuators (20, 22) may be made of any soft materials such as silicone (e.g., ECOFLEX™ 00-30). Exemplary actuators are linear actuators (22) and locomotive actuators (20) (FIG. 8E).

Base (10) may contain linear actuatable arms (22) (e.g., 2, 3, 4, or more, in particular 4) (FIGS. 8E, 16) that can move in a specific direction (e.g., horizontally inwards against the probe) to move transducer probe (30) in a selected direction (e.g., translated horizontally, angled, or rotated). Based on the actuation distance, the tilt angle of the transducer can be changed (FIGS. 12A-12D).

Figure 10B:
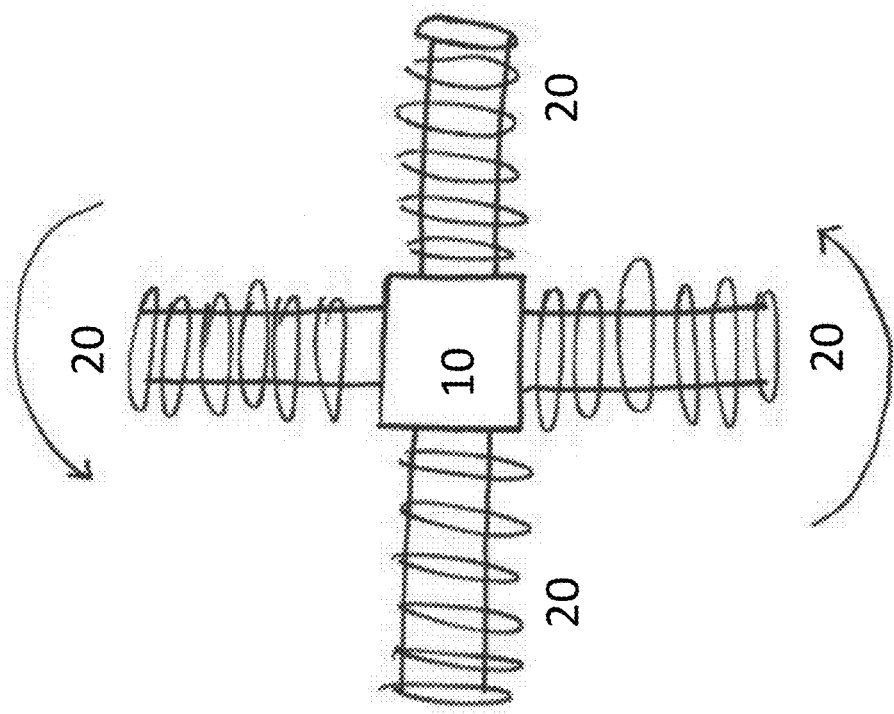
FIG. 10B is a schematic drawing of a base (10) connected to four soft robotic actuatable arms (20) that can rotate the angle of the base.
Figure 10A:
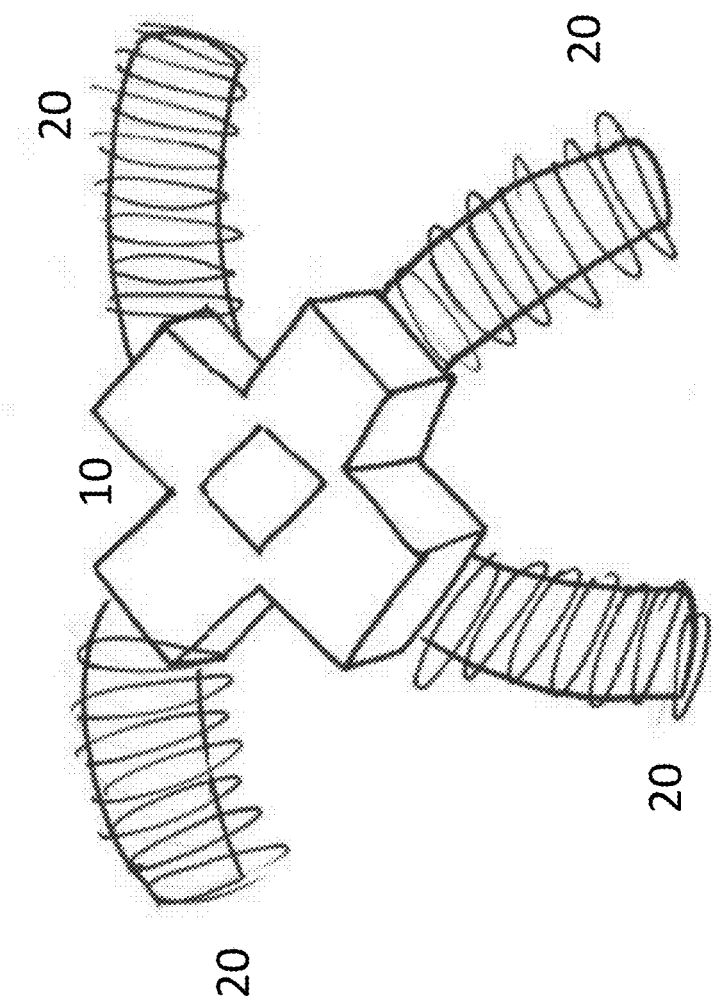
FIG. 10A is a schematic drawing of a base (10) connected to four soft robotic actuatable arms (20) that can adjust the height of the base.

Base (10) may contain locomotive actuators (20), which may reside in base (10) but are vertical and provide vertical adjustment when actuated (FIGS. 7, 8A-8E, 9A-9C). The locomotion actuators (e.g., 2, 3, 4, or more, in particular 4) provide multiple types of movements, such as elongation, bending, rotation and locomotion (FIGS. 10A-10B). Based on these movements, the vertical height of transducer (30) may be adjusted. Additionally, the rotation angle and position can be changed when the soft robot moves. Locomotive actuators (20) may also provide grip as they can bend around their target, such as a body part. Suction cups may be added at the bottom of the actuators to hold the device in place. The actuators may protrude radially from the base such as in a spider-like configuration (FIG. 3A).

Top Frame

The transducer holder may also include a top frame an additional attachment that can be added as a top component to a base. An example is top frame (16) shown in FIGS. 11A and 11B. Top frame (16) may be adjustable in height (e.g., from about 10 mm to about 30 cm). Top frame (16) can hold the transducer from a fixed point from which angular deflection of the transducer can occur. Top frame (16) may be made of any light and rigid material (e.g., plastic, such as ABS). The inner piece may be configured to split in half so that top frame (16) can be snapped around probe (30). Top frame (16) may also contain arms (24) that control the distance between top frame (16) and base (10). Arms (24) may be extendable or collapsible in order to adjust their length. Arms (24) may collapse by a telescopic mechanism and be precisely controlled, e.g., with stop screws or hydraulic pressure. Alternatively, top frame (16) may be configured to move up and down, while arms (24) remain fixed.

Top frame (16) or base (10) may also contain rotary guide frame (60) (FIG. 3B), which allows rotation around the rotary track and linear motion in the slot of the ultrasound transducer to achieve a proper rotation angle. Each side of top frame (16) may be, for example, from about 10 mm to about 30 cm.

Top frame (16) can be connected to base (10) by, e.g., screws, friction fit (e.g., arms (24) can be inserted into a receiving port on base (10), snaps, or other attachment methods. Arms (24) may extend from about 10 mm to about 150 mm in length.

Belt

A belt or strap may be used to hold assembly (70) in place and secure it to a subject, e.g., if the patient is not stationary or the ultrasound transducer holder does not easily rest on the surface being probed with the ultrasound transducer. A belt may allow the scan to be conducted in both dynamic and static positions. The belt may be composed of any suitable material (e.g., VELCRO®) to affix the device to a patient. A belt or strap may also be used to affix the ultrasound transducer to holder or base (10). VELCRO®, snaps, friction fit, or any other retaining mechanism may also be used.

Sensors

The ultrasound transducer holder and the ultrasound transducer may include sensors that allow the ultrasound transducer assembly to measure different sensory conditions (e.g., pressure and position). The sensors may be thin and flexible and can give feedback on sensory parameters (e.g., pressure). For example, actuatable arms (20) can be modified with pressure sensor (34) that allows the detection and mapping of pressure against the skin. Pressure sensor (34) may be attached or affixed to the surface of one or more of actuatable arms (20) or transducer (30) as a modular component or integrated into base (10), e.g., into a surface of base (10). The ultrasound transducer may also contain photo sensor (32), which can be used to track the position of transducer (30) (FIG. 3A).

The pressure sensor can constantly measure pressure exerted on the skin by the transducer assembly. If the pressure goes above or below a functional limit of performing an ultrasound (e.g., greater than or less than 0.001 psi, 0.005 psi, 0.01 psi, 0.05 psi, 0.1 psi, 0.2 psi, 0.3 psi, 0.4 psi, 0.5 psi, 0.6 psi, 0.7 psi, 0.8 psi, 0.9 psi, 1 psi, 2 psi, 3 psi, 4 psi, 5 psi, 6 psi, 7 psi, 8 psi, 9 psi, 10 psi, 20 psi, 30 psi, 40 psi, 50 psi, 60 psi, 70 psi, 80 psi, 90 psi, or 100 psi), the device can alert the user. Table 1 lists types of sensors that may be used with the devices described herein.

TABLE 1

Types of Sensors

| Sensors | Catalog # | Manufacturer | Supplier |
| --- | --- | --- | --- |
| Pressure | Flexiforce A301 | Tekscan | South Boston, MA, USA |
| Pressure | Flexiforce A401 | Tekscan | South Boston, MA, USA |
| Position sensor | Flexipot | Tekscan | South Boston, MA, USA |
| Photo sensor | PR-G Sensors | Keyence | Itasca, IL, USA |

Microprocessor

The ultrasound transducer holder may further include a microprocessor connected to the sensors. A microprocessor (e.g., Arduino Uno R3 from SparkFun, Niwot, Colo.) may be connected to the sensors by an electrical wire or wirelessly to interpret, characterize, and store data and information collected by sensors (32, 34). The microprocessor can take the input stimuli from the sensory data and convert that into an output decision (e.g., robotic motion). The microprocessor may also be used to control the actuation steps of the ultrasound transducer holder by initiating a series of pressurization and depressurization steps to provide the robotic motion of the arms. The computer algorithms of the microprocessor may be controlled (e.g., by a user interface) to initiate the arms to perform a desired movement or function. The microprocessor may also be used control one or more of the ultrasound parameters (e.g., pressure, angle, rotation, and tilt).

The microprocessor may contain a computational algorithm (FIG. 18) to enable sensory feedback of sensors (32, 34) on the device. For example, assembly (70) rests in a starting position. Upon initiation of the actuatable arms (e.g., locomotive and/or linear actuators), base (10) and probe (30) move to a new position or angle. Sensors (32, 34) may then collect information pertaining to the pressure, location, and orientation of ultrasound probe (30). This sensory information is then sent as feedback to the microprocessor. An ultrasound image(s) may then be captured by transducer probe (30) or, if necessary, the microprocessor may initiate new movements by locomotive actuators (20) to achieve a desired alignment or position.

Soft Robotics

The soft robotics structure of soft robotic actuatable arm (20, 22) may be made with elastic materials that provide flexibility, bendability, adjustability and customization of the gripping component. Examples of materials that can be used include two part silicone rubber (e.g., ECOFLEX™ 00-30 and ELASTOSIL® 4601), silicone (e.g., PDMS), rubber, latex, polyurethanes, various vulcanized rubber, and polymeric materials. Additionally, soft robotics provide larger degrees of freedom of motion and higher sensitivity to enable grasping delicate objects as compared to hard robotics. Soft robots are safer, more flexible, inexpensive, and can conform better to the objects.

Figure 7:
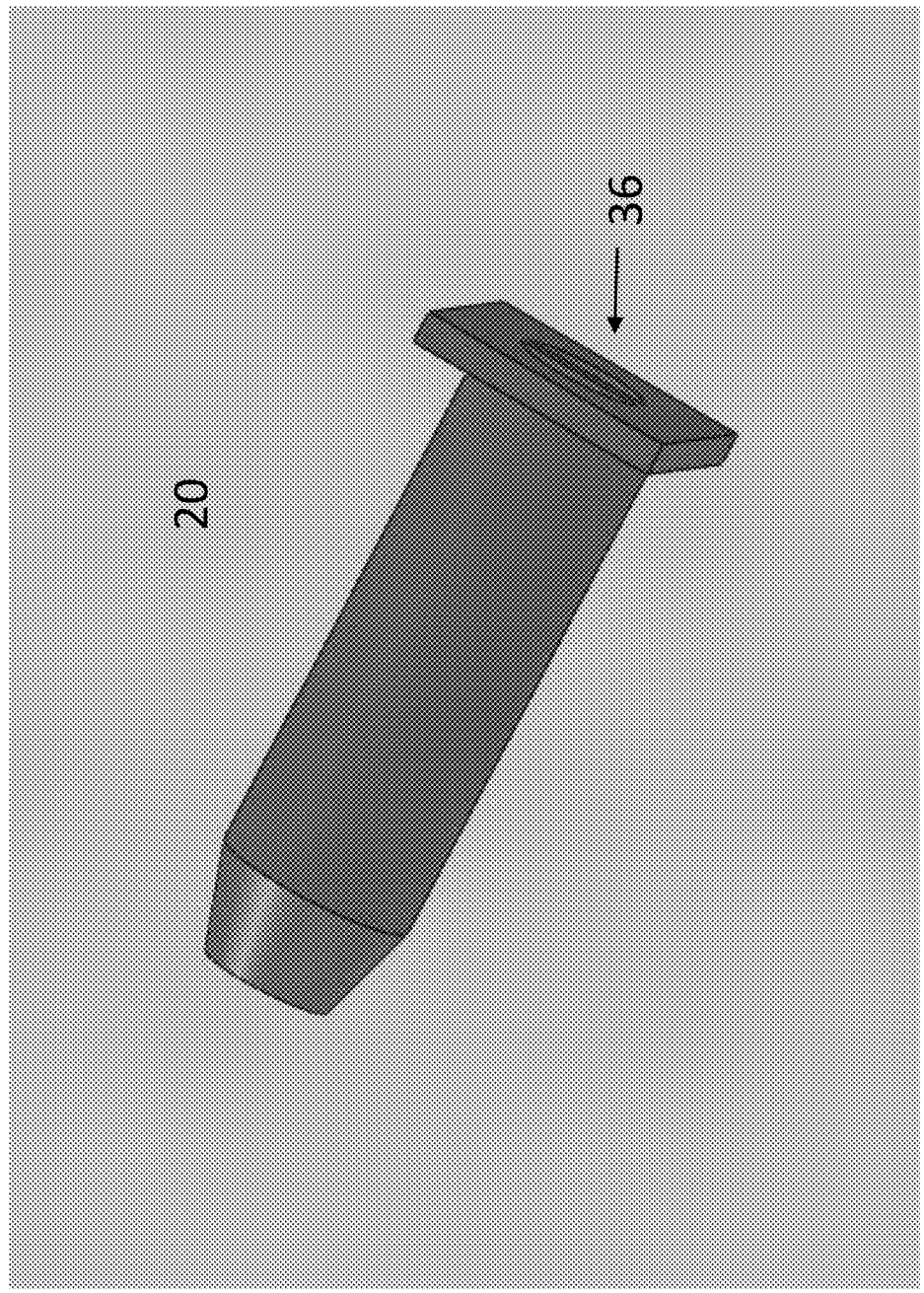
FIG. 7 is a schematic drawing of a soft robotic actuatable arm (20).
Figure 9C:
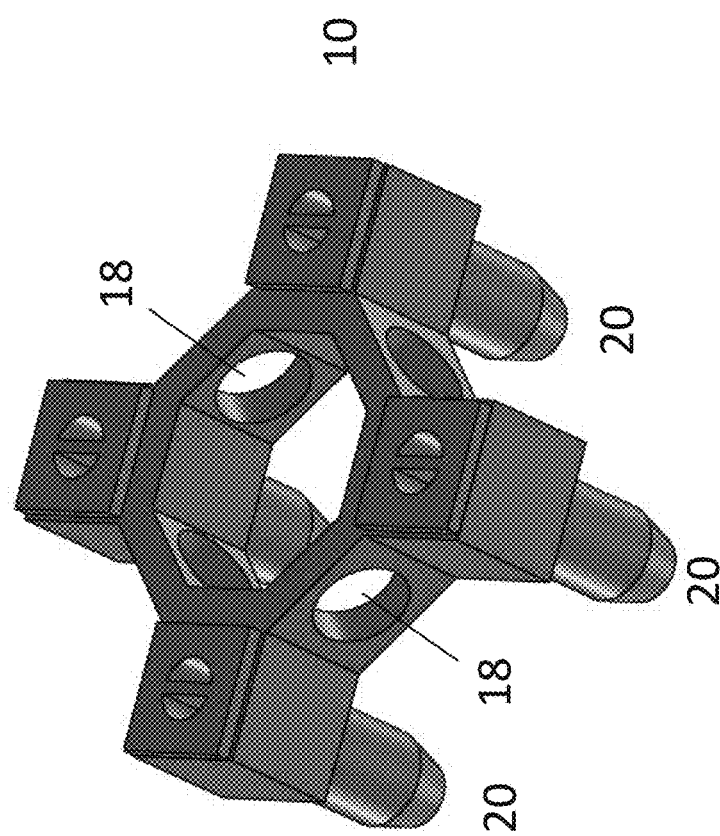
FIGS. 9A-9C are schematic drawings showing a side perspective view (FIG. 9A), a bottom perspective view (FIG. 9B), and a top perspective view (FIG. 9C) of the ultrasound transducer base (10) connected to four soft robotic actuatable arms (20).
Figure 9A:
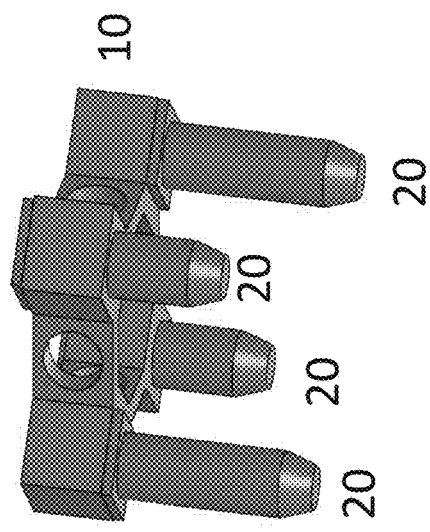
Figure 9B:
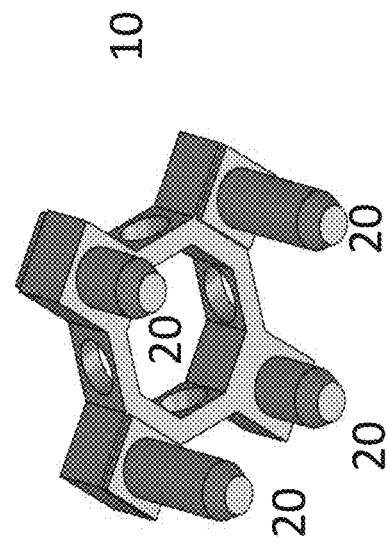
Figure 18:
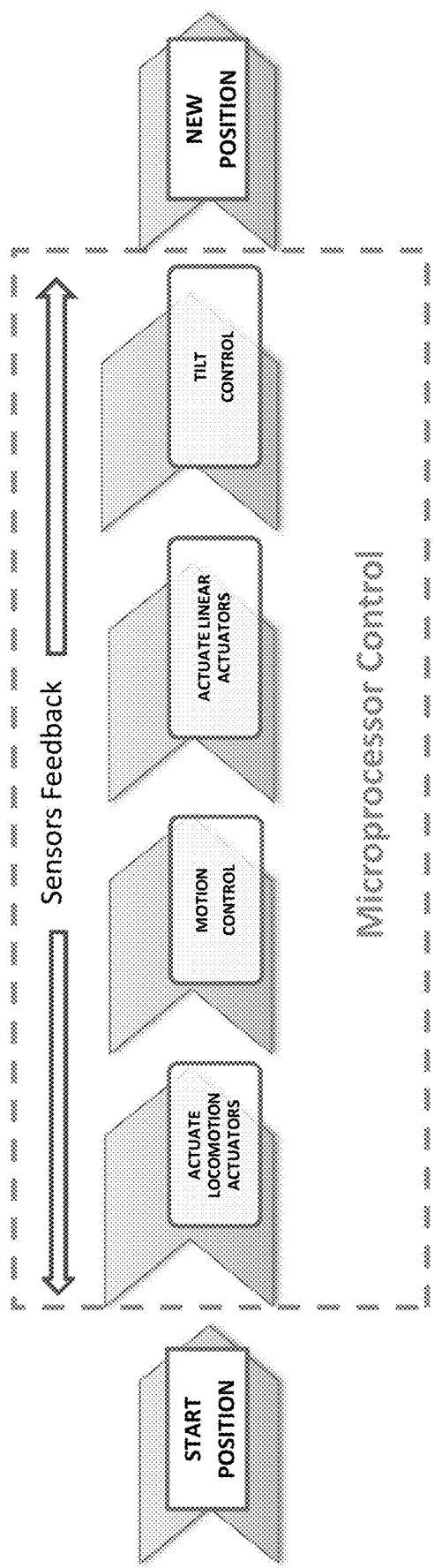
FIG. 18 is a flow chart depicting how a microprocessor can be used to control various movements via sensory feedback.

Soft robotics can make use of elastic polymers to provide the variability of functional movements achieved by actuatable arms (20, 22). Soft robotics also entails using pneumatically driven actuators that are fluidly coupled to sealed chambers. The chambers fill with air, through a pressurizing inlet and expand arms (20) in specific directions. Pressurizing inlet (36) is connected to a source of air (FIG. 7). The actuation pressure, materials, rubber skin thickness, mechanical properties, and restraints of various areas of actuatable arms (20, 22) can be adjusted to modulate the functionality of ultrasound transducer holder (10). The molded body of actuatable arm (20, 22) can be made from a soft silicone material in the durometer range of Shore 00-30 to Shore 30A. Motion may be generated by inflating one or more air chambers (38) of the locomotion actuators (FIGS. 15A-15B). As soft robotic arms (20, 22) create motion, the position of base (10) and transducer probe (30) changes (FIG. 18).

Soft robotic actuators have been described, for example, in U.S. Pat. No. 9,464,642, the disclosure of which is herein incorporated by reference. A fluid source, such as a squeeze bulb, gas canister, or air pump may be connected to actuatable arms (20, 22) by, e.g., a hose, and used to fill air chambers (38) and actuate arms (20, 22). The fluid source may provide a series of pressurization and depressurizations to control the precise movements of actuatable arms (20, 22). The pressurization and depressurization steps may be computationally controlled (e.g., by a microprocessor) to perform the specific movements and motions of arms (20, 22). The pressure settings of the fluid source (e.g., increase or decrease) may also be modulated to control these pressurization and depressurization steps. Each arm (20, 22) may have a single inlet, each of which is connected to a single fluid source. Alternatively, arm (20, 22) may have more than one (e.g., 2, 3, 4, and 5) inlets to receive a fluid or two or more arms (20, 22), or each arm (20, 22), may be actuated by a separate fluid source.

Strain is a measurement of relative deformation of a material from a reference configuration. A deformation results from a stress induced by an applied force, such as a pressurizing force from air, a fluid or gas. A material with a high elastic modulus will not deform as much under the same stress as a material with a low elastic modulus. Materials with a lower stiffness (e.g., Young's Modulus) or elastic modulus are more expansible or extensible, while materials with a higher stiffness or elastic modulus are less expansible or extensible and can function as the skin layer in actuatable arm (20).

Furthermore, different portions, layers, or compartments of the molded body of actuatable arms (20, 22) may be composed of one or more different materials or materials with different thicknesses, so as to provide different mechanical properties in different regions of arms (20, 22). A layer of the material may be comprised of two or more different materials (e.g., rubber embedded with graphite). By using additives to layers or regions, the stiffness of the material can be increased or decreased. By tailoring the mechanical properties of each portion, layer, or compartment, arms (20, 22) can be customized to conform to specific shapes.

Uses

The soft robotic holder, when coupled with an ultrasound transducer is used to perform an ultrasound procedure on a target object. The target object may be any body part on a subject, (e.g., a human). The assembly is prepared by affixing ultrasound transducer probe (30) into base (10), e.g., with a strap. Assembly (70) is then placed on the body, and may be affixed, e.g., with a strap, to a specific body part. An ultrasound technician may physically move, or a microprocessor may be programmed to move, ultrasound transducer assembly (70) by initiating a series of pressurization and depressurization steps to move actuatable arms (20) on base (10). By actuating arms (20), the assembly can crawl or walk on the body to a specific location. The technician obtains the correct pressure, alignment, rotation, and tilt to achieve an acceptable quality of an ultrasound image. Each parameter is controlled by different combinations of physical movements of actuatable arms (20, 22) and, if desired, rotary guide frame (60). For example, the actuators may move linearly to progress forwards, backwards, left, or right on the target object. Additionally, linear actuators (22) may push against probe (30) to control the tilt angle or orientation of the probe. Rotary guide frame (60) may rotate probe (30) or actuators (20) may curl or bend around an object to provide torque and rotate the base (FIG. 10B). Actuators (20), top frame (16), or top frame arms (24) may be adjustable in height, thereby applying more or less pressure on the target (FIGS. 11A-11B, 14A-14B). Photo (32) or pressure (34) sensors may be used as a feedback mechanism to map the pressure applied to the skin and the relative orientation of the probe on the target object. A combination of changes in height and rotation may adjust the tilt angle of the transducer probe.

Either during, or after moving the probe to a desired location, the ultrasound transducer emits ultrasonic waves to initiate imaging of the target object. Multiple imaging scans can be performed while moving the probe to test the quality of a given probe orientation. The technician can then move assembly (70) to a new location to acquire more ultrasound images until the procedure is complete.

Figure 17:
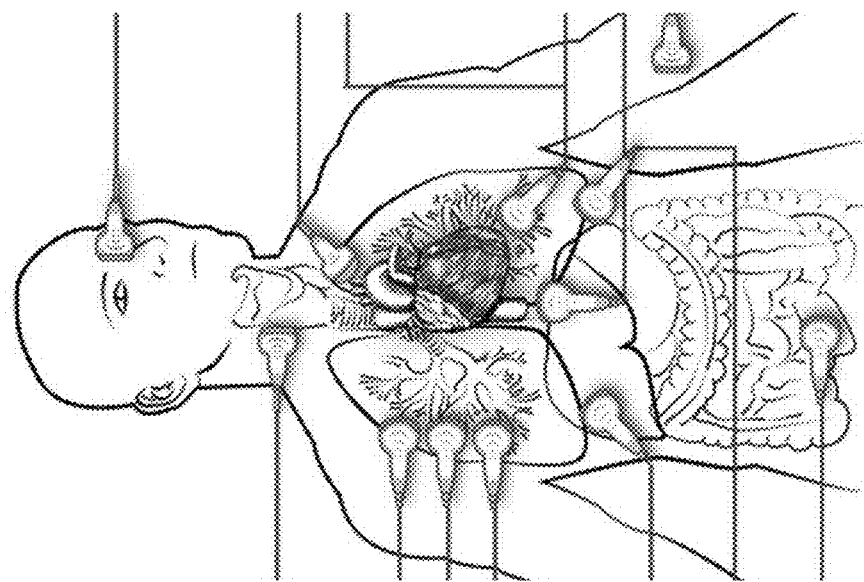
FIG. 17 is a diagram showing various areas on the body where ultrasound imaging may be performed.

The devices and methods described herein may be useful for any type of ultrasound procedure. They may be useful to view any type of body part (e.g., blood vessels (see, e.g., FIG. 14A-14B), internal organs (e.g., heart, breast, lung, liver, kidney, stomach, and spleen), tendons, and internal cavities (e.g., abdomen)). It can be used to look at the walls of the abdomen to check for any fluids or as part of routine prenatal care to track fetal development during pregnancy. Body parts that may be visualized by ultrasound imaging are shown in FIG. 17.

The soft robotic holder and ultrasound transducer may also be used for diagnosing patients suffering from contagious diseases or epidemics where the diagnostic test can be done autonomously using ultrasound imaging.

The ultrasound holder and ultrasound transducer may also be used as a training mechanism to train or assist an ultrasound technician in order to reduce time and to collect automated images.

The ultrasound holder and ultrasound transducer may also be used to apply ultrasound therapy to a patient, e.g., during physical therapy.

The ultrasound transducer holder and ultrasound transducer can also be used in anesthesiology procedures to guide a user during needle injection, in angiology procedures to diagnose arterial and venous disease, in emergency medicine to assess pericardial tamponade after trauma (e.g., Focused Assessment with Sonography for Trauma (FAST)), in gastroenterology procedures to probe inflammation of solid organs, in head and neck surgery to visualize tumors and lesions, in neonatology to assess intracerebral structural abnormalities, in neurology to assess blood flow in the carotid arteries, in obstetrics to track fetal development, in ophthalmology to image the eyes, in pulmonology to visualize endobronchial lesions and nodes prior to aspiration, in urology to determine bladder fluid retention, in musculoskeletal medicine to image fractures, and in cardiovascular medicine to assess arterial obstructions and deep vein thrombosis.

Common musculoskeletal areas or conditions that can be diagnosed or imaged with ultrasound include, for example, tendon tears, tendinitis of the rotator cuff in the shoulder, Achilles tendon in the ankle and other tendons throughout the body, muscle tears, masses or fluid collections, ligament sprains or tears, inflammation or fluid (effusions) within the bursae and joints, early changes of rheumatoid arthritis, nerve entrapments, such as carpal tunnel syndrome, benign and malignant soft tissue tumors, ganglion cysts, hernias, foreign bodies in the soft tissues (such as splinters or glass), dislocations of the hip in infants, fluid in a painful hip joint in children, neck muscle abnormalities in infants with torticollis (neck twisting), and soft tissue masses (lumps/bumps) in children.

The ultrasound transducer holder can be used with an ultrasound transducer to assist in analyzing the condition of a joint, ligaments, muscles and nerves, for example, while the patient is at rest or in motion. This can be useful for producing an image when the patient is in pain or experiences spasms during particular motions. The transducer holder is portable and allows for hands-free operation of the ultrasound device, such that a technologist would not be required to hold and manipulate the transducer in a certain position in order to administer the ultrasound. For example, the ultrasound transducer holder may be used with an ultrasound transducer to monitor rotator cuff disease or tendon tears of the ankle. A series of imaging tests assists in diagnosing the symptoms and predicting positions that cause pain using artificial intelligence and data mining from captured images. The ultrasound transducer holder may be used with an ultrasound transducer that delivers ultrasound therapeutic energy. This may be used for rehabilitation of chronic pains. The ultrasound holder can be used with an ultrasound transducer to map a path for the ultrasound therapy.

The ultrasound transducer holder may be used with an ultrasound transducer during a stress test, which involves obtaining a stress echocardiogram. During a stress echocardiogram, the ultrasound transducer measures Left Ventricular Ejection Fraction (LVEF) and Left Ventricular Outflow Tract (LVOT) when the patient is exercising and at rest. In a stress echo test, the echocardiogram is obtained at rest in a sleep position on left side. The patient will then typically exercise on a treadmill and an echocardiogram is obtained after exercise at rest in the sleep position again. The ultrasound scan is obtained while the patient is in stationary position following the exercise to measure the Left Ventricular Ejection Fraction (LVEF) and Left Ventricular Outflow Tract (LVOT). The holder can be attached to the patient with the soft robotic holder and used to position the ultrasound transducer, such that a real time ultrasound scan can be taken while the patient is in motion or at rest.

The ultrasound transducer holder may be used to position an ultrasound transducer in an ultrasound procedure during a pandemic, epidemic, or contagious disease scenario so that the ultrasound technologist does not have to be in the room with the patient during the ultrasound procedure as a result of the automation of the transducer holder (e.g., when there are an insufficient number of medical personnel to perform the procedure or when there may be an exposure risk to the medical personnel when coming into contact with the patient).

EXAMPLES

The following examples are intended to illustrate, rather than limit, the disclosure.

Example 1. Actuation of a Soft Robotic Ultrasound Transducer Holder

The soft robotic actuator (20, 22) has an air inlet (36) and two semicircular air channels (38) and can move in different directions based on air flow. If one chamber (38) is pressurized, then the soft actuator (20, 22) bends. If both air chambers (38) are pressurized, then the soft actuator (20, 22) elongates and gives linear actuation. If various actuators are controlled with an on/off pulse, the actuators can walk.

Linear actuators (22) are placed in the holder base horizontally. The holder has a center recess of 50.8 mm on the octagon and the probe has a diameter of 25.4 mm, so there is a clearance gap of 25.4 mm to which probe (30) can be tilted. The angle relationship is given in Tables 2 and 3.

TABLE 2

Tilt angle with linear actuator movement

| | Actuator Movement (mm) | | | |
|---|---|---|---|---|
| | 6.35 | 12.70 | 19.05 | 25.4 |
| Tilt Angle, degrees | 4° | 8° | 12° | 16° |

TABLE 3

Vertical height adjustment with tilt angle

| | Tilt Angle, degrees | | | |
|---|---|---|---|---|
| | 4° | 8° | 12° | 16° |
| Height change (mm) | 0.34 | 1.36 | 3.05 | 5.41 |

Movement of assembly (70) occurs by actuating the locomotive actuators (20) on the bottom of base (10). These four actuators elongate when inflated in both chambers and retract when deflated in both chambers thus giving a crawling motion. Actuating one chamber (38) of actuator (20) causes a bending motion around uninflated chamber (38), thus raising the height and giving an inchworm like movement. Other movements include climbing and rotating. All these movements may be achieved using air inflation in chamber (38). The actuator is 50.8 mm long and can be inflated up to 88.9 mm long to perform a movement up to 12.7 mm.

Example 2. Performing an Echocardiogram

Figure 1A:
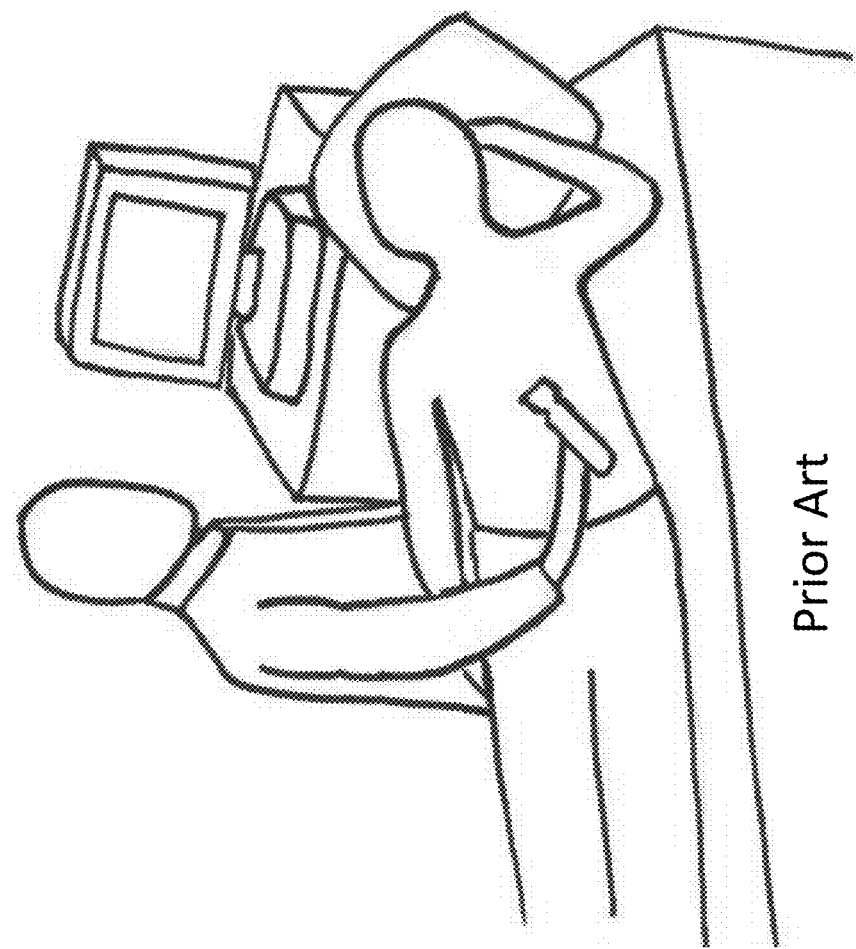
FIG. 1A is a schematic drawing of a technician performing an ultrasound on a patient.
Figure 1B:
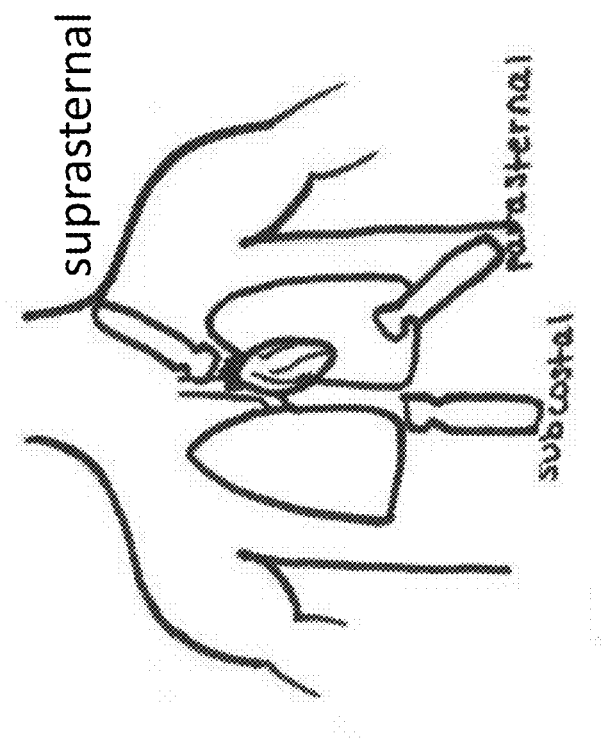
FIG. 1B is a schematic drawing of different transducer placements to view certain regions of the cardiovascular system.

The devices described herein may be used to perform an echocardiogram to obtain different ultrasound image views of the heart. A technician or operator will mount ultrasound transducer (30) in base (10) and/or top frame (16). Ring (18) in the center of top frame (16) will snap around probe (30) to keep it in place. Top frame (16) is adjustable in height so probe (30) can be adjusted up or down in the assembly during mounting. Once transducer probe (30) is mounted in assembly (70), the assembly can be placed on the chest of a subject above the heart. A strap or belt can be used if needed to hold maintain general position. The air source is then turned on and probe (30) can be directed to move to a specific location by interacting with the microprocessor. The assembly can be manipulated to tilt transducer (30) to obtain ultrasound images of the heart at different angles. Three views of the heart that can be imaged include the parasternal long axis view, which looks at the left side of the heart, the subcostal view, which look at the four chambers, and the suprasternal view, which looks at the aorta (FIGS. 1B, 17). The air actuation of locomotion actuators (20) can move the probe to various locations required for the echocardiogram. Once the position is fixed, the height can be adjusted to obtain the correct focal area for imaging by adjusting locomotion actuators (20) and using pressure mapping sensors (34) to the correct position vertically. Top frame (16) can also be adjusted again to obtain the desired correct height. The air actuation of linear actuators (22) can tilt probe (30) to obtain the images at various tilt angles. With this examination, a series of images can be generated with position and pressure mapping feedback (FIG. 18). This can be then recorded and used again for a repetitive evaluation.

Example 3. Evaluating Musculoskeletal Conditions in Motion

An ultrasound technician attaches the transducer holder to a patient with musculoskeletal pain. The patient reports significant pain and spasms in his shoulder when raising his arm. The straps on the transducer holder keep the transducer probe in close contact with the patient's shoulder, such as when the patient raises their arm. The transducer holder positions the ultrasound transducer in close proximity to a joint, ligaments, muscles, and/or nerves of the shoulder of the patient, e.g., while the patient is in motion, thereby assisting the technician in analyzing the patient's condition while freeing the hands of the technician to perform other tasks during the procedure. A series of imaging tests can be performed that assist the technician with diagnosing the patient's condition. The results of the imaging tests can be used, e.g., in combination with artificial intelligence and data mining from the captured images, to predict positions that cause pain. The technologist can then program the transducer to provide ultrasound therapeutic treatment in the painful area. The ultrasound holder can be used to map a path for the ultrasound therapeutic treatment. The therapeutic approach can be used, e.g., over one or move sessions, to treat a patient with acute pain or with chronic pain.

Example 4. Automated Ultrasound Scan During Contagious Disease Scenario

During a pandemic or an epidemic scenario, e.g., where there may be a risk of exposure of medical staff to an infective agent when they come into direct contact with an infected patient, the holder can be used to provide a hands-free solution to obtain ultrasound scans remotely without the need for a technologist to be present in the room with the patient. The technologist can operate the transducer holder to position an ultrasound transducer remotely during an ultrasound scan of the patient, e.g., by using a computer to dictate the motions and movements of the holder and the transducer probe during the scan.

Other Embodiments

All publications, patents, and patent applications mentioned in the above specification are hereby incorporated by reference to the same extent as if each individual publication, patent or patent application was specifically and individually indicated to be incorporated by reference in its entirety.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. An ultrasound transducer holder comprising:
 a) a base for holding and/or positioning an ultrasound transducer, the base comprising a center hole configured to surround the transducer;
 b) a plurality of actuatable arms attached to the base and configured to contact a subject, each actuatable arm comprising:
  i) a flexible molded body having a plurality of interconnected chambers disposed within the molded body, and
  ii) a pressurizing inlet that is configured to receive fluid into the plurality of interconnected chambers, wherein the molded body is configured to expand when the plurality of interconnected chambers are pressurized by the fluid, thereby moving the base and/or the transducer upon actuation of the arm; and
 c) a plurality of linear actuators disposed substantially horizontally within the base and configured to protrude at least partially within the center hole, wherein each linear actuator is configured to contact the transducer and adjust a tilt angle of the transducer upon actuation.

2. The ultrasound transducer holder of claim 1, further comprising the ultrasound transducer, wherein the ultrasound transducer contacts the base.

3. The ultrasound transducer holder of claim 1, wherein the flexible molded body comprises an elastically extensible material and a strain-limiting material having a higher elastic modulus relative to the elastically extensible material.

4. The ultrasound transducer holder of claim 1, further comprising a sensor.

5. The ultrasound transducer holder of claim 4, wherein the sensor is a pressure sensor or a photo.

6. The ultrasound transducer holder of claim 5, wherein the photo sensor is located on the ultrasound transducer and/or the pressure sensor is located on one of the plurality of actuatable arms.

7. The ultrasound transducer holder of claim 1, wherein the center hole has a diameter of about 10 mm to about 100 mm.

8. The ultrasound transducer holder of claim 1, further comprising a top frame or a rotary guide frame attached to the base.

9. The ultrasound transducer holder of claim 8, wherein:
 the top frame is adjustable in height;
 the rotary guide frame is attached to the top frame; and/or
 the rotary guide frame controls a rotation angle of the ultrasound transducer.

10. The ultrasound transducer holder of claim 1, wherein the plurality of actuatable arms are adjustable in height.

11. The ultrasound transducer holder of claim 1, further comprising a microprocessor.

12. The ultrasound transducer holder of claim 11, wherein the microprocessor controls at least one of the plurality of actuatable arms to manipulate an ultrasound parameter.

13. The ultrasound transducer holder of claim 12, wherein the ultrasound parameter is one or more of pressure, alignment, rotation angle, and tilt angle.

14. The ultrasound transducer holder of claim 1, further comprising the ultrasound transducer, wherein the ultrasound transducer is affixed to the base.

15. The ultrasound transducer holder of claim 14, further comprising a strap, hook-and-loop snaps, friction fit, or fastener that affixes the ultrasound transducer to the base.

16. The ultrasound transducer holder of claim 1, further comprising a strap, hook-and-loop, snaps, or friction fit configured to affix the ultrasound transducer to the subject.

17. The ultrasound transducer holder of claim 1, wherein the base comprises 2, 3, 4, four or more actuatable arms; or wherein the base is rigid.

18. The ultrasound transducer holder of claim 17, wherein the actuatable arms are equidistantly positioned on the base relative to each other.

19. A method of performing ultrasound imaging using the ultrasound transducer holder of claim 1 and an ultrasound transducer, the method comprising:
  initiating a series of pressurizations and depressurizations of the plurality of actuatable arms that brings the ultrasound transducer into proximity to a target object, and emitting ultrasound waves from the ultrasound transducer to produce an image of the target object.

20. The method of claim 19, wherein the series of pressurizations and depressurizations adjust a height, pressure, alignment, rotation angle, or tilt angle of the holder and the transducer relative to the target object;
  wherein the series of pressurizations and depressurizations move the ultrasound transducer relative to the target object; or
  wherein the method comprises manipulating the holder so as to move the transducer, thereby achieving an ultrasound parameter.

21. The method of claim 19, wherein the ultrasound imaging produces an echocardiogram of a patient's heart or a musculoskeletal image.

22. A kit comprising the ultrasound transducer holder of claim 1 and an ultrasound transducer.

* * * * *